United States Patent
Sasaki et al.

(10) Patent No.: US 9,080,190 B2
(45) Date of Patent: Jul. 14, 2015

(54) METHOD FOR PRODUCING CADAVERINE

(75) Inventors: Nanami Sasaki, Kamakura (JP); Takashi Mimitsuka, Kamakura (JP); Hideki Sawai, Tokai (JP); Kenji Sawai, Kamakura (JP)

(73) Assignee: Toray Industries, Inc. (JP)

( * ) Notice: Subject to any disclaimer, the term of this patent is extended or adjusted under 35 U.S.C. 154(b) by 170 days.

(21) Appl. No.: 13/992,081

(22) PCT Filed: Dec. 8, 2011

(86) PCT No.: PCT/JP2011/078391
§ 371 (c)(1),
(2), (4) Date: Jul. 15, 2013

(87) PCT Pub. No.: WO2012/077741
PCT Pub. Date: Jun. 14, 2012

(65) Prior Publication Data
US 2013/0323800 A1    Dec. 5, 2013

(30) Foreign Application Priority Data

Dec. 8, 2010  (JP) .................................. 2010-273340

(51) Int. Cl.
C12P 13/00    (2006.01)

(52) U.S. Cl.
CPC ....... *C12P 13/001* (2013.01); *C12Y 401/01018* (2013.01)

(58) Field of Classification Search
None
See application file for complete search history.

(56) References Cited

FOREIGN PATENT DOCUMENTS

| JP | 53-086089 | 7/1978 |
|---|---|---|
| JP | 03-201978 | 9/1991 |
| JP | 2002-223770 | 8/2002 |
| JP | 2004-222569 | 8/2004 |
| JP | 2008-104453 | 5/2008 |
| JP | 2009-28045 | 2/2009 |
| JP | 2009-29872 | 2/2009 |
| JP | 2009-207495 | 9/2009 |
| WO | 2007/113127 | 10/2007 |
| WO | 2008/092720 | 8/2008 |
| WO | 2008/101850 | 8/2008 |

OTHER PUBLICATIONS

Kind, S. et al., "Systems-Wide Metabolic Pathway Engineering in *Corynebacterium glutamicum* for Bio-Based Production of Diaminopentane," *Metabolic Engineering*, 2010, vol. 12, pp. 341-351 (1 page Abstract).

Ekwealor, I.A. et al., "Screening of UV-Irradiated and S-2-aminoethyl-L-cysteine Resistant Mutants of *Bacillus megaterium* for Improved Lysine Accumulation," *African Journal of Biotechnology*, Nov. 16, 2006, vol. 5, No. 22, pp. 2312-2314.

Pisoni, R.L. et al., "Detection and Characteriszation of a Transport System Mediating Cysteamine Entry into Human Fibroblast Lysosomes," *The Journal of Biological Chemistry*, 1995, vol. 270, No. 3, pp. 1179-1184.

Corpillo, D. et al., "Induction and Characterization of a Novel Amine Oxidase from the Yeast *Kluyveromyces marxianus*," *Yeast*, 2003, vol. 20, pp. 369-379.

*Primary Examiner* — Suzanne M Noakes
*Assistant Examiner* — Jae W Lee
(74) *Attorney, Agent, or Firm* — DLA Piper LLP (US)

(57) ABSTRACT

A method produces cadaverine more efficiently and at a higher yield than production methods by the conventional fermentation methods. The method includes culturing coryneform bacterium/bacteria having an ability to produce cadaverine and having a resistance to 2,2'-thiobis(ethylamine). Preferably, the coryneform bacterium/bacteria has/have lysine decarboxylase activity and, preferably, the coryneform bacterium/bacteria has/have homoserine auxotrophy and/or a resistance to S-(2-aminoethyl)-L-cysteine.

11 Claims, No Drawings

```
                              SEQUENCE LISTING

<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagaattct taaacctcag catctgcccc                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaaggatcca aaggacttgt ttaccgacgc                                          30

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaaccgcggc ctgaatcgcc ccatcatcc                                           29

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaaccatggc cccttgtatt actg                                                24
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaaccatgga cgttattgca a                                                 21

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaccgcggt tattttttgc tttcttcttt                                        30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acagaattcg tggccctggt cgtacagaa                                         29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catctcgagt tagcgtccgg tgcctgcat                                         29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgacatcatc ttcacctgcc                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcaggtgaa gatgatgtcg                                                   20

<210> SEQ ID NO 11
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acggtcgact cgcagaataa ataaatcctg gtg                                33

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgaggcctg agaggcggtt tgcgtattgg a                                  31

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttggaacgcg tcccagtggc                                               20

<210> SEQ ID NO 14
<211> LENGTH: 421
<212> TYPE: PRT
<213> ORGANISM: Corynebacterium glutamicum

<400> SEQUENCE: 14

Val Ala Leu Val Val Gln Lys Tyr Gly Gly Ser Ser Leu Glu Ser Ala
 1               5                  10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
```

-continued

```
                    180                 185                 190
Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
        210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
                355                 360                 365

Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
                420
```

METHOD FOR PRODUCING CADAVERINE

SEQUENCE LISTING

This application contains a Sequence Listing which has been submitted in ASCII format via EFS-Web and is hereby incorporated by reference in its entirety. Said ASCII copy, created on Jun. 11, 2013, is named TAN-13-1127_SL.txt and is 6,943 bytes in size.

TECHNICAL FIELD

This disclosure relates to a method of producing cadaverine by using coryneform bacterium/bacteria having an ability to produce cadaverine.

BACKGROUND

Cadaverine has a diamine structure and is also called 1,5-pentanediamine or pentamethylenediamine and so on. Since cadaverine has recently been focused on as a raw material monomer for polyamide, mass production of cadaverine is demanded. Known examples of the method of producing cadaverine include a fermentation method using a coryneform bacterium, more specifically, a production method of cadaverine by fermentation of a coryneform bacterium having an ability to produce cadaverine and having a strengthened ability to synthesize lysine which is a precursor of cadaverine (see JP 2004-222569 A, JP 2002-223770 A, WO 2007/113127, WO 2008/101850 and Stefaine Kind, *Metabolic Engineering* (2010), vol. 12, pages 341-351), and a production method of cadaverine by fermentation of a coryneform bacterium which lysine decarboxylase activity is strengthened by increasing the number of copies of lysine decarboxylase gene (see WO 2008/092720).

It could be helpful to provide a process of producing cadaverine more efficiently and at a higher yield than production methods of cadaverine by conventional fermentation methods.

SUMMARY

We found that coryneform bacterium/bacteria having an ability to produce cadaverine and having a resistance to 2,2'-thiobis(ethylamine) is/are useful as cadaverine-producing bacterium/bacteria.

We thus provide:

(1) A method for producing cadaverine, the method comprising culturing a coryneform bacterium/bacteria having an ability to produce cadaverine and having a resistance to 2,2'-thiobis(ethylamine).

(2) The method for producing cadaverine, according to (1), wherein the coryneform bacterium/bacteria has/have a resistance to 2,2'-thiobis(ethylamine) having a concentration of not less than 250 mM.

(3) The method for producing cadaverine, according to (1) or (2), wherein the coryneform bacterium/bacteria has/have lysine decarboxylase activity.

(4) The method for producing cadaverine, according to any one of (1) to (3), wherein the coryneform bacterium/bacteria is/are selected from the group consisting of the genus *Corynebacterium* and the genus *Brevibacterium*.

(5) The method for producing cadaverine, according to any one of (1) to (4), wherein the coryneform bacterium/bacteria has/have homoserine auxotrophy and/or a resistance to S-(2-aminoethyl)-L-cystein.

Cadaverine can be produced more efficiently and at a higher yield than production methods of cadaverine by conventional fermentation methods

DETAILED DESCRIPTION

Coryneform bacterium/bacteria is/are used in our methods. Coryneform bacteria are aerobic gram-positive bacilli and also include bacteria which had previously been classified in the genus *Brevibacterium*, but have now been integrated into the genus *Corynebacterium* (Int. J. Syst., Bacteriol., (1981) 41, p. 225). Coryneform bacteria also include the bacteria belonging to the genus *Brevibacterium* which is very close to the genus *Corynebacterium*.

Examples of such coryneform bacteria include *Corynebacterium acetoacidophylum*, *Corynebacterium acetoglutamicum*, *Corynebacterium alkanolyticum*, *Corynebacterium callunae*, *Corynebacterium glutamicum*, *Corynebacterium lilium*, *Corynebacterium mellassecola*, *Corynebacterium thermoaminogenes*, *Corynebacterium efficiens*, *Corynebacterium herculis*, *Brevivacterium divaricatum*, *Brevivacterium flavum*, *Brevivacterium immariophilum*, *Brevivacterium lactofermentum*, *Brevivacterium roseum*, *Brevivacterium saccharolyticum*, *Brevivacterium thiogenitalis*, *Corynebacterium ammoniagenes*, *Brevivacterium album*, *Brevivacterium cerinum* and *Microbacterium ammoniaphilum*.

Concrete examples of strains of the respective coryneform bacteria include *Corynebacterium acetoacidophylum* ATCC13870, *Corynebacterium acetoglutamicum* ATCC15806, *Corynebacterium alkanolyticum* ATCC21511, *Corynebacterium callunae* ATCC15991, *Corynebacterium glutamicum* ATCC13020, ATCC13020 and ATCC13060, *Corynebacterium lilium* ATCC15990, *Corynebacterium mellassecola* ATCC17965, *Corynebacterium efficiens* AJ12340 (accession No. FERM BP-1539), *Corynebacterium herculis* ATCC13868, *Brevivacterium divaricatum* ATCC14020, *Brevivacterium flavum* ATCC13826, ATCC14067 and AJ12418 (accession No. FERM BP-2205), *Brevivacterium immariophilum* ATCC14068, *Brevivacterium lactofermentum* ATCC13869, *Brevivacterium roseum* ATCC13825, *Brevivacterium saccharolyticum* ATCC14066, *Brevivacterium thiogenitalis* ATCC19240, *Corynebacterium ammoniagenes* ATCC6871 and ATCC6872, *Brevivacterium album* ATCC15111, *Brevivacterium cerinum* ATCC15112 and *Microbacterium ammoniaphilum* ATCC15354.

The above-described coryneform bacteria are available from, for example, American Type Culture Collection (ATCC). That is, a corresponding accession number is given to each strain in ATCC and described in the catalogue of ATCC, and each strain can be furnished by reference to this number.

As the coryneform bacterium/bacteria having an ability to produce cadaverine, coryneform bacterium/bacteria which acquired lysine decarboxylase activity by externally introducing a polynucleotide encoding lysine decarboxylase is/are preferably used. Coryneform bacteria can produce cadaverine by using lysine as a raw material and decarboxylating the lysine, as long as the coryneform bacteria have lysine decarboxylase activity.

The lysine decarboxylase is preferably L-lysine decarboxylase. The origin of the lysine decarboxylase is not restricted, and preferred examples of the lysine decarboxylase include those derived from *Bacillus halodurans*, *Bacillus subtilis*, *Escherichia coli*, *Selenomonas ruminamtium*, *Vibrio cholerae*, *Vibrio parahaemolyticus*, *Streptomyces coelicolor*, *Streptomyces pilosus*, *Eikenella corrodens*, *Eubacterium*

*acidaminophilum, Salmonella typhimurium, Hafnia alvei, Neisseria meningitidis, Thermoplasma acidophilum* and *Pyrococcus abyssi*. The lysine decarboxylase is more preferably the one derived from *E. coli* whose safety has been confirmed. The amino acid sequences and the base sequences coding therefor of these lysine decarboxylases (hereinafter also referred to as "LDC") are registered in a database (GenBank). For example, the base sequence of the LDC gene derived from *E. coli* that may preferably be employed is registered under GenBank Accession No. M76411.

The nucleic acid sequences of the gene encoding the lysine decarboxylase may be redesigned in consideration of the codon usage of the coryneform bacterium/bacteria used. As mentioned above, the gene of the lysine decarboxylase derived from the above-described each organism is registered in a database (GenBank), and the base sequence of each LDC gene may easily be found by carrying out a search using the name of the organism and the lysine decarboxylase as the keywords.

In addition to the naturally occurring LDC gene of the above-mentioned each organism species, the gene encoding lysine decarboxylase also include polynucleotides whose base sequences are the same as respective base sequences of the naturally occurring LDC gene except that one or several bases are substituted, deleted, inserted and/or added, as long as their functions are maintained. The term "several" herein means normally 1 to 40, preferably about 1 to 30, more preferably about 1 to 20, especially preferably about 1 to 10, most preferably about 1 to 5. Further, examples of the gene encoding the lysine decarboxylase include polynucleotide that entirely or partially hybridizes with the polynucleotide constituting the gene or with the complementary strands thereof under stringent conditions, as long as their functions are maintained. The term "polynucleotide that hybridizes under stringent conditions" herein means a nucleic acid sequence that hybridizes with a probe(s) having one or more nucleic acid sequences each having at least 20, preferably 25, more preferably at least 30 continuous sequences arbitrarily selected from the original base sequence, when a known hybridization technique (Current Protocols I Molecular Biology edit. Ausbel et al., (1987) Publish. John Wily & Sons Section 6.3-6.4) or the like is applied. The stringent conditions herein can be achieved, for example, by performing hybridization in the presence of 50% formamide at a temperature of 37° C., at 42° C. for more stringent condition, or at 65° C. for even more stringent condition, followed by washing with 0.1× to 2×SSC solution (composition of 1×SSC solution: 150 mM sodium chloride, 15 mM sodium citrate). The polynucleotide encoding the lysine decarboxylase may be a polynucleotide having a sequence identity of normally not less than 85%, preferably not less than 90%, more preferably not less than 95%, even more preferably not less than 99% to the original sequence, as long as the functions are maintained.

The term "sequence identity" herein means the value calculated by aligning the two sequences such that the number of matched bases between the two base sequences is the maximum (a gap(s) is(are) inserted as required), and by dividing the number of matched bases by the number of total bases. In cases where the numbers of bases between the two sequences are different, the number of matched bases is divided by the number of bases of the longer sequence. Software calculating the sequence identity is well known and freely available. The gene encoding lysine decarboxylase may be obtained either from an organism other than the original host or by subjecting a gene obtained from the original host to in vitro mutagenesis or site-directed mutagenesis, which is well-known.

In cases where the gene encoding a lysine decarboxylase (hereinafter also referred to as "lysine decarboxylase gene" or "LDC gene", but the gene is not restricted to naturally occurring gene as described above) is introduced to coryneform bacterium/bacteria, the lysine decarboxylase gene may be retained in a plasmid maintained outside the chromosome of coryneform bacterium/bacteria, or may be incorporated and retained in the chromosome of coryneform bacterium/bacteria.

In cases where the lysine decarboxylase gene is incorporated in the chromosome of coryneform bacterium/bacteria, the lysine decarboxylase gene can be introduced to the chromosome of coryneform bacterium/bacteria by using transposon and by homologous recombination or by the transposition ability of the transposon itself. Construction and confirmation of the gene sequence to be introduced are carried out according to well-known molecular biological techniques, and one may refer to, for example, Sambrook et al., Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glovered. 1985); F. M. Ausubel et al. (eds), Current Protocols in Molecular Biology (1994) John Wiley & Sons, Inc.; and PCR Technology: Principles and Application for DNA Amplication, H. Erlich, ed., Stockton Press, or the like.

The method of introducing the gene construct to the coryneform bacterium/bacteria is not restricted and the gene construct may be introduced by the protoplast method (Gene, (1985), 39, pp. 281-286), electroporation method (Bio/Technology, (1989), 7, 1067-1070) or the like.

The coryneform bacterium/bacteria in which a foreign LDC gene is introduced and which has/have an ability to produce cadaverine, is/are known as described in, for example, JP 2004-222569 A (see Reference Example below).

Next, coryneform bacterium/bacteria having a resistance to 2,2'-thiobisethylamine will now be described concretely.

The 2,2'-thiobisethylamine is a strong alkaline chemical compound represented by the structural formula: $NH_2$—$(CH_2)_2$—$S$—$(CH_2)_2$—$NH_2$. Having a resistance to 2,2'-thiobisethylamine means that the bacterium/bacteria has/have a property to grow faster than the wild-type strain on a medium containing 2,2'-thiobisethylamine. Specifically, although the wild-type strain cannot form colonies on a plate medium containing 2,2'-thiobisethylamine having a concentration of not less than 200 mM, the strain forming colonies two to three days later can be judged to have a resistance to 2,2'-thiobisethylamine. The concentration of thiobisethylamine to which the coryneform bacterium/bacteria has/have a resistance on a plate medium is not restricted, and the concentration thereof is preferably not less than 250 mM, more preferably not less than 300 mM, still more preferably not less than 400 mM.

The medium containing 2,2'-thiobisethylamine to evaluate resistance of coryneform bacterium/bacteria to 2,2'-thiobisethylamine is not restricted as long as it is a medium on which coryneform bacterium/bacteria can be cultured, and the medium is preferably a minimal medium to which an amino acid or the like is not added, and more preferably a minimal medium shown in Table 1.

TABLE 1

| | |
|---|---|
| Glucose | 5 g |
| $(NH_4)_2SO_4$ | 7 g |
| $NH_4Cl$ | 1 g |
| $MgSO_4 \cdot 7H_2O$ | 0.4 g |
| NaCl | 0.525 g |
| $KH_2PO_4$ | 3 g |

TABLE 1-continued

| | |
|---|---|
| $Na_2HPO_4$ | 6 g |
| $CaCl_2 \cdot 2H_2O$ | 7.35 mg |
| $FeSO_2 \cdot 7H_2O$ | 20 mg |
| $MnSO_4 \cdot 4H_2O$ | 2 mg |
| $ZnSO_4 \cdot 7H_2O$ | 0.02 mg |
| $CuSO_4 \cdot 5H_2O$ | 0.54 mg |
| $(NH_4)_6Mo_7O_{24} \cdot 4H_2O$ | 0.08 mg |
| $Na_2MoO_4 \cdot 2H_2O$ | 0.176 mg |
| $Na_2B_4O_7 \cdot 7H_2O$ | 0.176 mg |
| $FeCl_3 \cdot 6H_2O$ | 1.74 mg |
| $MnCl_2 \cdot 4H_2O$ | 0.0144 mg |
| thiamine•HCl | 1 mg |
| Biotin | 30 µg |
| Protocatechuic acid | 15 mg |
| | up to 1 L |

The method of giving resistance to 2,2'-thiobisethylamine to coryneform bacterium/bacteria is not restricted and, for example, the method may be one which causes some mutation to the chromosome of the parent strain. Examples of the technique which introduces a mutation to the chromosome include a method of introducing a mutation by irradiation of UV, laser or the like, and a method using a mutagen such as methyl ethanesulfonate (EMS), nitrosoguanidine (NTG), sodium 4-dimethylaminobenzenediazosulfonate (DAPA). A natural mutation occurred in culturing coryneform bacterium/bacteria may also be used. As the method of providing coryneform bacterium/bacteria having an ability to produce cadaverine and having a resistance to 2,2'-thiobisethylamine, the resistance may be given to coryneform bacterium/bacteria having an ability to produce cadaverine, or as mentioned above, the ability to produce cadaverine may be given to the coryneform bacterium/bacteria to which the resistance was given. The above-described mutagenesis treatment may be carried out under well known conditions used in mutagenesis treatments of microorganism. For example, in case of UV irradiation, the dose of radiation depends on the distance from light source, and the irradiation is usually carried out for 10 seconds to 30 minutes. In case of the treatment with the above-described mutagen such as NTG, the concentration of the mutagen during the treatment is, for example, 100 µg/ml to 2 µg/ml, preferably 300 µg/ml to 1.3 µg/ml, and the treatment can be carried out in a culture medium having this concentration, for example, for 12 hours to 48 hours.

After such mutagenesis treatment, the coryneform bacterium/bacteria having a resistance to 2,2'-thiobisethylamine can be obtained by culturing the treated coryneform bacterium/bacteria on the above-described medium for evaluating a resistance to 2,2'-thiobisethylamine, and by screening a strain(s) which acquired the resistance to 2,2'-thiobisethylamine. As is described concretely in the Examples below, a plurality of strains acquiring a resistance to 2,2'-thiobisethylamine are obtained by the treatment with NTG, which clearly shows that the strain having a resistance to 2,2'-thiobisethylamine can be produced reproducibly by the mutagenesis treatment.

Furthermore, coryneform bacterium/bacteria is/are preferably mutant(s) having an improved ability to produce lysine. As the mutant having an improved ability to produce lysine, for example, the mutant which feedback inhibition is relieved by L-lysine or L-threonine can be used. Examples of the method of obtaining such mutants include, for example, a method for obtaining the mutant from mutants which are selected by using a resistance to S-(2-aminoethyl)-L-cystein (AEC) as indices after carrying out the same mutagenesis procedure for wild-type strain as the above example, and which acquired an ability to produce L-lysine (see JP 2004-222569 A). Whether the bacterium/bacteria has/have a resistance to AEC or not can be judged by whether the bacterium/bacteria proliferate(s) or not after culturing the bacterium/bacteria on a minimal agar medium containing 50 µg/ml of AEC at 30° C. for 24 hours as described in JP 2004-222569 A.

Alternatively, the more preferable method of giving the wild-type strain a resistance to AEC is a method using a genetic engineering method. The method using a genetic engineering method is not restricted and examples thereof include, for example, a method using a recombinant DNA which is replicable in a coryneform bacterium, or a method by which the desired gene in the chromosome is recombined by homologous recombination. For example, a resistance to S-(2-aminoethyl)-L-cystein can be acquired by having a mutated aspartokinase gene in which the 311st amino acid residue is substituted by an amino acid other than Thr in the amino acid sequence shown in SEQ ID NO: 14 (the gene may be hereinafter referred to as "desensitized type AK gene". The more preferable genetic engineering method is a method by which the AK gene in the chromosome of the coryneform bacterium is recombined with the desensitized type AK gene by homologous recombination. Furthermore, the well-known techniques of introducing the desired mutation to the AK gene (for example, site-directed mutagenesis) can be used for the desensitized type AK gene, and a kit therefor is commercially available.

Examples of the mutant having an improved ability to produce lysine include a homoserine-auxotrophic mutant in addition to the AEC-resistant mutant. Although the wild-type strain does not have homoserine auxotrophy, examples of the method of obtaining the homoserine-auxotrophic strain include a method of obtaining the strain from mutants selected by using homoserine auxotrophy as indices, for example, after carrying out the same mutagenesis procedure for the wild-type strain as the above example, and which acquired an ability to produce L-lysine; and a method of making homoserine dehydrogenase activity of a coryneform bacterium be deficient by a genetic engineering method (JP 2004-222569 A).

Examples of the more preferable method for giving the wild-type strain homoserine auxotrophy include a method of making homoserine dehydrogenase activity be deficient by inserting another gene into homoserine dehydrogenase gene in the chromosome (hereinafter referred to as "HOM gene" for short) by homologous recombination. The other gene is not restricted, and preferably a LDC gene, and a cassette comprising the LDC gene and a promoter which can express the gene constitutively in the wild-type strain is more preferred.

Cadaverine is produced by culturing coryneform bacterium/bacteria having an ability to produce the cadaverine and having a resistance to 2,2'-thiobisethylamine. Examples of the culture method include batch culture, fed-batch culture and continuous culture. In the cases of continuous culture, continuous culture is preferably carried out by a known method as described in JP 2008-104453 A.

As a culture medium of producing cadaverine, a normal nutrient medium comprising an assimilable carbon source, nitrogen source, inorganic salt and/or the like may be used. Examples of the carbon source which may be used include saccharides such as glucose, fructose, sucrose, maltose and starch hydrolysates; alcohols such as ethanol; and organic acids such as acetic acid, lactic acid and succinic acid. Examples of the nitrogen source which may be used include ammonia; inorganic and organic ammonium salts such as ammonium chloride, ammonium sulfate, ammonium carbonate and ammonium acetate; nitrogen-containing compounds such as urea; and nitrogen-containing organic substances such as meat extracts, yeast extracts, corn steep liquor and soybean hydrolysates. Examples of the inorganic salt which may be used include potassium dihydrogen phosphate, dipotassium hydrogen phosphate, ammonium sulfate, sodium chloride, magnesium sulfate and calcium carbonate. Further, as required, micronutrients such as biotin, thiamine, vitamin B6 and the like may be added. Medium additives such as meat extracts, yeast extracts, corn steep liquor, casamino acids and the like may be used as alternatives to these micronutrients.

Lysine which is a precursor of cadaverine may be preliminarily added to the culture medium. In cases where lysine is preliminarily added to the culture medium, lysine is incorporated into coryneform bacterium/bacteria, and lysine is used as a substrate and converted to cadaverine by lysine decarboxylase, so that the production efficiency of cadaverine can be enhanced. In the cases where lysine is preliminarily added to the culture medium, the concentration of lysine in the culture medium is not restricted, and the concentration of lysine is preferably one at which the growth of the coryneform bacterium/bacteria is not adversely affected and lysine decarboxylase is not inhibited. More concretely, the concentration is preferably 0.01 to 2 M.

The lysine to be added is preferably L-lysine. The lysine to be added may be either in the free form or a salt of lysine, and preferably a salt of lysine. The salt of lysine is preferably lysine hydrochloride or a lysine dicarboxylate derived from the dicarboxylic acid described later. Preferred concrete examples of lysine dicarboxylate include lysine adipate, lysine sebacate, lysine 1,12-dodecanedicarboxylate, lysine succinate, lysine isophthalate and lysine terephthalate, and more preferred concrete examples of lysine dicarboxylate include lysine adipate.

The culture conditions are not restricted, and culturing is carried out under aerobic conditions, for example, with shaking or by deep aeration stirring culture. The culture temperature is generally 25° C. to 42° C., preferably 28° C. to 38° C. The culture period is normally 1 day to 6 days.

In cases where the culture pH is adjusted to alkaline, ammonia is preferably used, and in cases where the culture pH is adjusted to acidic, hydrochloric acid or dicarboxylic acid is preferably used, and dicarboxylic acid is more preferably used. It is preferred to use the neutralizer to control the culture pH to 5 to 8, more preferably 6.5 to 7.5. The state of the neutralizer is not restricted, and the neutralizer may be used as a gas, liquid, solid or an aqueous solution. The neutralizer is especially preferably an aqueous solution.

The dicarboxylic acid to be preferably used as the neutralizer is not restricted and the dicarboxylic acid is preferably a dicarboxylic acid having substantially no functional group other than the above-described two carboxyl groups. The functional group herein means a reactive group which reacts, during polyamide polymerization reaction (under reaction conditions wherein, for example, the reaction temperature is 250 to 270° C., the pressure is 10 to 20 kg/cm², and the reaction time is 1 to 5 hour(s)), with an amino group or carboxyl group to cause branching of the polymer or reduction in the degree of crystallinity of the polymer (to a degree of crystallinity of not more than 80%). Examples of the functional group include the amino group and carboxyl group, and other examples of the functional group include acidic groups (e.g., the sulfonic acid group, phosphate group and phenolic hydroxyl group), basic groups (e.g., the hydrazino group), protonic polar groups (e.g., the hydroxyl group), cleavable groups (e.g., the epoxy group and peroxide group) and other highly reactive groups (e.g., isocyanate group). On the other hand, halogen substituents, aromatic substituents, ether groups, ester groups, amide groups and the like are not included in the functional group in this description since their reactivity is low.

The dicarboxylic acid is more preferably a dicarboxylic acid represented by Formula (1), (2) or (3) below.

$$HOOC-(CH_2)_m-COOH \qquad (1)$$

(wherein in Formula (1), m=0 to 16).

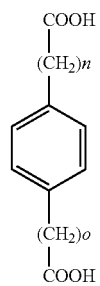

(wherein in Formula (2), n, o=0 to 16).

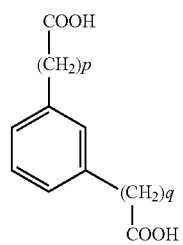

(wherein in Formula (3), p, q=0 to 16).

The dicarboxylic acid is still more preferably adipic acid, sebacic acid, 1,12-dodecanedicarboxylic acid, succinic acid, isophthalic acid or terephthalic acid.

Cadaverine in the culture medium exists in the free state or as a salt of cadaverine (these are collectively referred to as "cadaverine"). To collect cadaverine in the culture medium, the coryneform bacterium/bacteria is/are first removed from the culture medium. In this case, the coryneform bacterium/bacteria and culture supernatant may be separated (the method of separating bacterium/bacteria is precipitation, centrifugation or membrane filtration separation) after the coryneform bacterium/bacteria proliferate(s) and the fermentation proceeds well, or the bacterium/bacteria may be separated, retained or immobilized by using support or the like from the beginning. The method of collecting cadaverine from the culture medium which the bacterium/bacteria was/were removed and which contains cadaverine, are well known per se, and cadaverine may be collected as cadaverine dicarboxylate by crystallization as described in JP 2009-207495 A. Alternatively, cadaverine in the free form may be purified and collected using an NF membrane as described in JP 2009-29872 A. Alternatively, cadaverine in the free form may be collected by extraction with a polar organic solvent and by distillation as described in JP 2009-28045 A.

EXAMPLES

Our methods will now be described below in detail by way of Examples and Comparative Examples.

Reference Example 1

Method of Analysis of Concentrations of Cadaverine and Lysine by HPLC

To 25 µl of the sample to be analyzed, 25 µl of 1,4-diaminobutane (0.03 M), 150 µl of sodium hydrogen carbonate (0.075 M) and a solution of 2,4-dinitrofluorobenzene (0.2 M) in ethanol were added and the resulting mixture was mixed and incubated at 37° C. for 1 hour. A 50-µl aliquot of the above reaction solution was dissolved in 1 ml of acetonitrile and the resulting solution was centrifuged at 10,000 rpm for 5 minutes, followed by subjecting 10 µl of the supernatant to HPLC analysis.
Column used: CAPCELL PAK C18 (Shiseido)
Mobile phase: 0.1% (w/w) aqueous phosphate solution: acetonitrile=4.5:5.5
Detection: UV 360 nm

Reference Example 2

Preparation of *Corynebacterium glutamicum* which has L-Lysine Decarboxylation Activity and which is Deficient in Homoserine Ddehydrogenase Activity (TR-CAD1 Strain) (JP 2004-222569 A)

(1) Cloning of HOM Gene

The gene corresponding to the region of 300 amino acids from the N-terminal was cloned for making HOM activity be deficient.

By reference to the base sequence of the HOM gene (Accession No. BA000036) registered in the database (GenBank), oligonucleotide primers 5'-gaagaattctaaacctcagcatct-gcccc-3' (SEQ ID NO:1) and 5'-gaaggatccaaaggacttgtttaccgacgc-3' (SEQ ID NO:2) were synthesized. 0.2 µl of a solution of genomic DNA prepared from *Corynebacterium glutamicum* ATCC13032 according to a conventional method as an amplification template was placed, and each reagent was added to the 0.2-ml microcentrifuge tube such that the resulting mixture, in a total volume of 50 µl, contained each primer 20 pmol, Tris-HCl buffer pH 8.0 (20 mM), potassium chloride (2.5 mM), gelatin (100 µg/ml), each dNTP (50 µM) and LA Taq DNA polymerase (2 units) (manufactured by Takara Shuzo Co., Ltd.). Polymerase chain reaction (hereinafter referred to as PCR) was carried out using a thermal cycler manufactured by BioRad under the conditions of 30 cycles of: denaturation of DNA at 94° C. for 30 seconds, annealing of the primers at 55° C. for 30 seconds, and extension reaction of the DNA primers at 72° C. for 3 minutes. The PCR in the Reference Example was carried out under the above conditions unless otherwise specified. The product obtained by this PCR was subjected to electrophoresis in 1% agarose, and a DNA fragment of about 0.9 kb containing the HOM gene was excised from the gel, followed by being purified using the Geneclean kit (manufactured by BIO 101 Inc.). This fragment was digested with the restriction enzymes EcoRI and BamHI, and the obtained 0.9-kb EcoRI-BamHI fragment was inserted into the EcoRI/BamHI gap of pHSG298 (manufactured by Takara Shuzo Co., Ltd.) which had been preliminarily digested with EcoRI and BamHI, using the Ligation kit Ver. 1 (manufactured by Takara Shuzo Co., Ltd.). The obtained plasmid was designated pHOM1.

(2) Preparation of LDC Expression Cassette

First, the promoter of the kanamycin-resistant gene was cloned as a promoter for constitutional expression of LDC in *Corynebacterium glutamicum*.

By reference to the base sequence of pHSG299 (Accession No. M19415) registered in the database (GenBank), oligonucleotide primers 5'-gaaccgcggcctgaatcgccccatcatcc-3' (SEQ ID NO:3) and 5'-gaaccatggccccttgtattactg-3' (SEQ ID NO:4) were synthesized. Using the plasmid pHSG299 as an amplification template and the oligonucleotides (SEQ ID NO:3) (SEQ ID NO:4) as a primer set, PCR was carried out to obtain a product, which was then subjected to electrophoresis in 1.0% agarose gel. A DNA fragment of 0.3 kb containing the promoter region of the kanamycin-resistant gene was excised from the gel and purified using the Geneclean kit. This fragment was inserted into the gap in the plasmid vector pT7blue (manufactured by Novagen) using the Ligation kit Ver. 1, which gap had been prepared by digesting the vector with EcoRV and adding the base T to the 3'-end. Among the obtained plasmids, the plasmid which became a single fragment of 3.2 kb after digestion with restriction enzymes HindIII and SacII was designated pKMP1.

Thereafter, the LDC gene was cloned. By reference to the base sequence of the LDC gene (Accession No. M76411) registered in the database (GenBank), oligonucleotide primers 5'-gaaccatggacgttattgcaa-3' (SEQ ID NO:5) and 5'-gaac-cgcggttatttttttgctttcttcttt-3' (SEQ ID NO:6) were synthesized. Using a solution of genomic DNA prepared from *Escherichia coli* ATCC10798 according to a conventional method as an amplification template and the oligonucleotides (SEQ ID NOs:5) (SEQ ID NOs:6) as a primer set, PCR was carried out to obtain a product, which was then subjected to electrophoresis in 1.0% agarose gel. A DNA fragment of 2.1 kb containing the LDC gene was excised from the gel, and was purified using the Geneclean kit. This fragment was inserted into the gap in the plasmid vector pT7blue using the Ligation kit Ver. 1, which gap had been prepared by digesting the vector with EcoRV and adding the base T to the 3'-end. Among the obtained plasmids, the plasmid which became a single fragment of 4.0 kb after digestion with HindIII and NcoI was designated pCADA.

Finally, pKMP1 was digested with HindIII and NcoI, and the obtained product was subjected to electrophoresis in 1.2% agarose gel. A DNA fragment of 0.3 kb containing the promoter region of the kanamycin-resistant gene was excised from the gel, and was purified using the Geneclean kit. The thus obtained HindIII-NcoI fragment was inserted into the HindIII/NcoI gap of pCADA which had been preliminarily digested with HindIII and NcoI, using the Ligation kit Ver. 1. The obtained plasmid was designated pTM100.

(3) Destruction of HOM Gene and Preparation of LDC Gene Expression Vector pTM100 was digested with SacII, and the obtained product was subjected to electrophoresis in 1.0% agarose gel. A DNA fragment of 2.4 kb containing LDC expression cassette was excised from the gel and purified using the Geneclean kit. The thus obtained SacII fragment was inserted into the SacII gap of pHOM1 which had been preliminarily digested with SacII, using the Ligation kit Ver. 1. The obtained plasmid was designated pTM101.

(4) Incorporation of pTM101 into Chromosome

The plasmid pTM101 was introduced to the *Corynebacterium glutamicum* ATCC13032 (hereinafter referred to as ATCC13032 strain for short) by electroporation [FEMS Microbiology Letters, 65, p. 299 (1989)], and subjected to selection on LB agar medium (tryptone (10 g/l) (manufactured by Bacto), yeast extract (5 g/l) (manufactured by Bacto), sodium chloride (10 g/l)) supplemented with kanamycin (25 µg/ml).

From the thus selected transformant, a genomic DNA solution was prepared according to a conventional method. Using this genomic DNA as a template and the oligonucleotides (SEQ ID NO:5) (SEQ ID NO:6) as a primer set, PCR was carried out to obtain a product, which was then subjected to electrophoresis in 1.0% agarose gel. As a result, a single band of 2.1 kb was observed. By this result, it could be confirmed that the selected transformant has the LDC gene inserted at the HOM locus. This transformant was designated *Corynebacterium glutamicum* TR-CAD1 (hereinafter referred to as the TR-CAD1 strain for short).

It was confirmed that the 13032 strain did not have LDC activity, while the TR-CAD1 strain had LDC activity. The 13032 strain had HOM activity, while the TR-CAD1 strain was deficient in HOM activity. The 13032 strain did not exhibit homoserine auxotrophy, while the TR-CAD1 strain showed homoserine auxotrophy. Thus, *Corynebacterium glutamicum* TR-CAD 1 strain which has LDC activity and which is deficient in HOM activity (homoserine auxotrophy) was prepared.

Reference Example 3

Preparation of *Corynebacterium glutamicum* which has L-Lysine Decarboxylation Activity, Homoserine Auxotrophy and S-(2-aminoethyl)-L-Cystein Resistance (TR-CAD2 Strain) (JP 2004-222569 A)

(1) Preparation of Desensitized Type AK Gene

The AK gene was cloned to prepare desensitized type AK gene by introducing a mutation into AK gene.

By reference to the base sequence of the AK gene (Accession No. BA000036) registered in the database (GenBank), oligonucleotide primers 5'-acagaattcgtggccctggtcgtacagaa-3' (SEQ ID NO:7) and 5'-catctcgagttagcgtccggtgcctgcat-3' (SEQ ID NO:8) were synthesized. Using a solution of genomic DNA prepared from *Corynebacterium glutamicum* ATCC13032 according to a conventional method as an amplification template and the oligonucleotides (SEQ ID NO:7) (SEQ ID NO:8) as a primer set, PCR was carried out to obtain a product, which was then subjected to electrophoresis in 1.0% agarose gel. A DNA fragment of 1.3 kb containing the AK gene was excised from the gel, and was purified using the Geneclean kit. This fragment was digested with EcoRI and XhoI, and the obtained 1.3-kb EcoRI-XhoI fragment was inserted into the EcoRI/XhoI gap of pHSG396 (manufactured by Takara Shuzo Co., Ltd.) which had been preliminarily digested with EcoRI and XhoI, using the Ligation kit Ver. 1. The obtained plasmid was designated pAK1.

The oligonucleotide primer 5'-cgacatcatcttcacctgcc-3' (SEQ ID NO:9) and 5'-ggcaggtgaagatgatgtcg-3' (SEQ ID NO:10) were synthesized for mutating the 931st to 933rd acc (Thr) of the cloned AK gene to atg (IIe). The plasmid obtained by using QuikChange Site-Directed Mutagenesis Kit (manufactured by Stratagene Corporation), pAK1 as an amplification template and the oligonucleotides (SEQ ID NO:9) (SEQ ID NO:10) as a primer set was designated pTM102. The AK gene in the pTM102 was sequenced according to a conventional method to confirm that the 931st to 933rd acc (Thr) was mutated to atg (IIe) as intended and desensitized type AK gene was prepared.

(2) Incorporation of pTM102 into Chromosome

By reference to the base sequence of the pFK398 (Accession No, D29826) registered in the database (GenBank), oligonucleotide primers of chloramphenicol-resistant gene 5'-acggtcgactcgcagaataaataaatcctggtg-3' (SEQ ID NO:11) and 5'-atgaggcctgagaggcggtttgcgtattgga-3' (SEQ ID NO:12) were synthesized.

The plasmid pTM102 was introduced to the TR-CAD1 strain by electroporation, and subjected to selection on LB agar medium supplemented with kanamycin (25 μg/ml) and chloramphenicol (10 μg/ml).

From the thus selected transformant, a genomic DNA solution was prepared according to a conventional method. Using this genomic DNA as a template and the oligonucleotides (SEQ ID NO:11) (SEQ ID NO:12) as a primer set, PCR was carried out to obtain a product, which was then subjected to electrophoresis in 1.0% agarose gel. As a result, a single band of 1.0 kb was observed. By this result, it could be confirmed that the selected transformant has the chloramphenicol-resistant gene inserted at the AK locus. This transformant was designated *Corynebacterium glutamicum* TR-CAD2 (hereinafter referred to as the TR-CAD2 strain for short).

(3) Confirmation of Introduction of Desensitized Type AK Gene onto Chromosome of TR-CAD2 Strain By reference to the base sequence of the AK gene (Accession No. BA000036) registered in the database (GenBank), oligonucleotide primer 5'-ttggaacgcgtcccagtggc-3' (SEQ ID NO:13) in a 0.1-kb region upstream of the N-terminal of the AK was synthesized.

A genomic DNA solution was prepared from the TR-CAD2 strain according to a conventional method. Using this genomic DNA as a template and the oligonucleotides (SEQ ID NO:12) (SEQ ID NO:13) as a primer set, PCR was carried out to obtain a product, which was then subjected to electrophoresis in 1.0% agarose gel. A DNA fragment of 3.1 kb containing the AK gene and the chloramphenicol-resistant gene was excised from the gel, and was purified using the Geneclean kit. This fragment was inserted into the gap in the plasmid vector pT7blue using the Ligation kit Ver. 1, which gap had been prepared by digesting the vector with EcoRV and adding the base T to the 3'-end. The obtained plasmid was designated pAK2. The AK gene in the pAK2 was sequenced according to a conventional method to confirm that the intended mutation was included. Therefore, it could be confirmed that the desensitized type AK gene capable of being expressed on the chromosome was introduced into the TR-CAD2 strain. Thus, *Corynebacterium glutamicum* (TR-CAD2 strain) which has LDC activity, which is deficient in HOM activity (homoserine auxotrophy) and which has AEC resistance was prepared.

Example 1

Obtaining Coryneform Bacteria which have Ability to Produce Cadaverine and 2,2'-Thiobis(ethylamine) Resistance The obtained *Corynebacterium glutamicum* (TR-CAD1 strain) which has L-lysine decarboxylase activity and which became a homoserine auxotrophic mutant by making homoserine dehydrogenase activity be deficient, and *Corynebacterium glutamicum* (TR-CAD2 strain) which has L-lysine decarboxylase activity, which became a homoserine auxotrophic mutant by making homoserine dehydrogenase activity be deficient and which has S-(2-aminoethyl)-L-cystein resistance (AEC resistance) as described above were each precultured in 5 ml of BHI (Brain Heart Infusion) liquid medium overnight. Into a new BHI liquid medium, 2.5 ml of the obtained preculture medium was inoculated, and the strains were cultured until the turbidity (A600) reaches 1 to 2. After culturing, the bacteria were washed with Tris-maleate buffer twice, and the washed bacteria were suspended in 12 ml of Tris-maleate buffer. The obtained suspension was aliquoted in 900 μl volumes to test tubes, and 640 μg/ml of NTG solutions are added to each test tube. The obtained mixture was shaked vigorously at 30° C. for 40 minutes, and suspended in 2 ml of BHI medium and cooled on ice. The obtained suspension was washed with Tris-maleate buffer twice, 50 ml of BHI medium was added thereto and the resultant cultured at 28° C. overnight. The culture medium was washed with Tris-maleate buffer twice, and after the culture in mediums shown in Table 1 for 2 to 3 days, to which mediums 2,2'-thiobisethylamine in a concentration of 180 mM, 220 mM, 250 mM, 300 mM and 400 mM were added, the bacteria having formed the colonies were obtained as 2,2'-thiobisethylamine-resistant strains, and each strain was designated as TR-CADA1-C, TR-CADA1-0 to 6 strains, TR-CADA2-C, TR-CADA2-0 to 6 strains (Table 2). Furthermore, it was confirmed that the obtained resistant strains were cultured for 3 days in the medium which the resistant strains described above were obtained, and colonies were formed, that is 2,2'-thiobisethylamine resistance was given to the strains.

TR-CADA1-6 strain and TR-CADA2-5 strain have been deposited with National Institute of Technology and Evaluation (NITE) under accession No. NITE BP-1002 and NITE BP-1003 respectively.

TABLE 2

| | Medium conditions | | | | |
|---|---|---|---|---|---|
| Parent strains | 2,2-Thiobis ethylamine 180 mM | 2,2-Thiobis ethylamine 220 mM | 2,2-Thiobis ethylamine 250 mM | 2,2-Thiobis ethylamine 300 mM | 2,2-Thiobis ethylamine 400 mM |
| TR-CADA1 | TR-CADA1-C | TR-CADA1-0 | TR-CADA1-1 TR-CADA1-2 | TR-CADA1-3 TR-CADA1-4 | TR-CADA1-5 TR-CADA1-6 |
| TR-CADA2 | TR-CADA2-C | TR-CADA2-0 | TR-CADA2-1 TR-CADA2-2 | TR-CADA2-3 TR-CADA2-4 | TR-CADA2-5 TR-CADA2-6 |

Examples 2 and 3 and Comparative Examples 1 and 2

Cadaverine fermentations were carried out by using TR-CADA1-1 to 6 strains (Example 2), TR-CADA2-1 to 6 (Example 3), TR-CADA1 strain (Comparative Example 1), TR-CADA1-0 strain (Comparative Example 2), TR-CADA2 (Comparative Example 3), TR-CADA2-0 (Comparative Example 4). Into 5 ml of sterilized BHI medium, one platinum loop of each strain was inoculated, and pre-preculture was carried out at 30° C. for 24 hours with shaking. The entire volume of the obtained pre-preculture was inoculated into 50 ml of the same medium as in the pre-preculture, and preculture was carried out at 30° C. with shaking amplitude of 30 cm at 120 rpm for 24 hours. Thereafter, the entire volume of the obtained preculture was inoculated into 950 ml of MMP medium shown in Table 3, and culture was carried out under aeration with sterilized air at 0.07 vvm at 30° C. at a stirring blade rotation speed of 800 rpm at a controlled pH of 6.7 for 50 hours. As neutralizers, an aqueous sulfuric acid solution (3 M) and aqueous ammonia (3 M) were used.

TABLE 3

| | |
|---|---|
| Glucose | 50 g |
| $(NH_4)_2SO_4$ | 20 g |
| Bacto Peptone | 5 g |
| $KH_2PO_4$ | 2.5 g |
| $K_2HPO_4$ | 2.75 g |
| NaCl | 0.5 g |
| $MgSO_4 \cdot 7H_2O$ | 0.75 g |
| $CaCl_2 \cdot 2H_2O$ | 0.05 g |

TABLE 3-continued

| | |
|---|---|
| $FeSO_4 \cdot 7H_2O$ | 0.01 g |
| $MnSO_4 \cdot 4$ to $6H_2O$ | 1 mg |
| Biotin | 0.5 mg |
| Tiamine•HCl | 7 mg |
| L-homoserine | 0.5 g |
| | up to 1 L |

After completion of the culture, the bacteria were removed by centrifugation at 4° C. at 8,000 rpm for 10 minutes, followed by recovering the culture supernatant. Cadaverine and lysine in this culture supernatant were analyzed by HPLC. To measure the glucose concentration, "Glucose Test Wako C" (registered trademark) (manufactured by Wako Pure Chemical Industries, Ltd.) was used. The yield of cadaverine relative to glucose consumption (weight of cadaverine produced/weight of glucose consumed)×100(%)) was calculated. The results are shown in Table 4.

TABLE 4

| | | Amount of accumulated cadaverine [g/L] | Amount of accumulated lysine [g/L] | Yield of cadaverine relative to glucose consumption [%] |
|---|---|---|---|---|
| Comparative Example 1 | TR-CADA1 | 5.6 | 1.2 | 11.2 |
| Comparative Example 2 | TR-CADA1-C | 5.7 | 1.4 | 10.9 |
| Example 2 | TR-CADA1-0 | 6.2 | 0.8 | 11.8 |
| | TR-CADA1-1 | 7.5 | 0.1 | 14.3 |
| | TR-CADA1-2 | 7.7 | 0.2 | 14.5 |
| | TR-CADA1-3 | 7.3 | 0.1 | 14.1 |
| | TR-CADA1-4 | 7.6 | 0 | 14.1 |
| | TR-CADA1-5 | 7.6 | 0.1 | 14.2 |
| | TR-CADA1-6 | 7.7 | 0 | 14.3 |
| Comparative Example 3 | TR-CADA2 | 6.4 | 0.2 | 12.8 |
| Comparative Example 4 | TR-CADA2-C | 6.6 | 0.3 | 12.3 |
| Example 3 | TR-CADA2-0 | 6.9 | 0.2 | 12.7 |
| | TR-CADA2-1 | 7.8 | 0 | 14.5 |
| | TR-CADA2-2 | 7.9 | 0 | 14.6 |
| | TR-CADA2-3 | 7.5 | 0 | 14.4 |
| | TR-CADA2-4 | 7.8 | 0 | 14.6 |
| | TR-CADA2-5 | 7.9 | 0 | 14.6 |
| | TR-CADA2-6 | 8.1 | 0 | 14.7 |

As a result, by comparison between Example 2 and Comparative Examples 1 and 2, and between Example 3 and Comparative Examples 3 and 4, it was revealed to improve that the concentration of accumulated cadaverine and the yield of cadaverine relative to glucose consumption were increased by giving 2,2'-thiobisethylamine resistance to the parent strain.

The collection of cadaverine from the obtained culture supernatant may be carried out by various known methods. The preferable known methods of collection will now be exemplified.

Reference Example 4

Collection of Cadaverine from Culture Supernatant

To the culture supernatant of the cadaverine fermentation liquid obtained in the above-mentioned method, 5 N of sodium hydroxide is added to adjust the pH to 13. Then, the resulting mixture is passed through nanofiltration membrane to remove inorganic salt components and trance residual bacteria, and the permeate through the nanofiltration membrane is collected. Thereafter, the collected permeate through the nanofiltration membrane is passed through a reverse osmosis membrane concentrated and collected until the concentration of cadaverine reaches about 18% by weight. Next, the collected concentrated solution is further concentrated under reduced pressure by a rotary evaporator or the like to remove water, and about 50% by weight of aqueous cadaverine solution is obtained. Then, an equal amount of chloroform is added to the solution, and cadaverine is extracted into the chloroform layer. Finally, the chloroform layer is distilled under reduced pressure (30 mmHg, 80° C.) to isolate free cadaverine.

INDUSTRIAL APPLICABILITY

Cadaverine can be produced industrially.
Accession Numbers
NITE BP-1002
NITE BP-1003

The invention claimed is:

1. A method of producing cadaverine comprising culturing coryneform bacteria having an ability to produce cadaverine and having a resistance to 2,2'-thiobis(ethylamine), wherein the production of cadaverine is increased relative to the amount produced by the parental strain which does not have a resistance to 2,2'-thiobis(ethylamine).

2. The method according to claim 1, wherein said coryneform bacteria have a resistance to 2,2'-thiobis(ethylamine) having a concentration of not less than 250 mM.

3. The method according to claim 1, wherein said coryneform bacteria have lysine decarboxylase activity.

4. The method according to claim 1, wherein said coryneform bacteria are selected from the group consisting of genus *Corynebacterium* and genus *Brevibacterium*.

5. The method according to claim 1, wherein said coryneform bacteria have homoserine auxotrophy and/or a resistance to S-(2-aminoethyl)-L-cystein.

6. The method according to claim 2, wherein said coryneform bacteria have lysine decarboxylase activity.

7. The method according to claim 2, wherein said coryneform bacteria are selected from the group consisting of genus *Corynebacterium* and genus *Brevibacterium*.

8. The method according to claim 3, wherein said coryneform bacteria are selected from the group consisting of genus *Corynebacterium* and genus *Brevibacterium*.

9. The method according to claim 2, wherein said coryneform bacteria have homoserine auxotrophy and/or a resistance to S-(2-aminoethyl)-L-cystein.

10. The method according to claim 3, wherein said coryneform bacteria have homoserine auxotrophy and/or a resistance to S-(2-aminoethyl)-L-cystein.

11. The method according to claim 4, wherein said coryneform bacteria have homoserine auxotrophy and/or a resistance to S-(2-aminoethyl)-L-cystein.

* * * * *